United States Patent [19]

Nehrbass

[11] 4,099,412
[45] Jul. 11, 1978

[54] METHOD OF MEASURING THE INSTANTANEOUS FLOW RATE OF URINE DISCHARGE

[76] Inventor: John Nehrbass, 4793 Lake Valley Dr., Lisle, Ill. 60532

[21] Appl. No.: 807,594

[22] Filed: Jun. 17, 1977

[51] Int. Cl.² .............................................. G01F 1/24
[52] U.S. Cl. ...................................... 73/209; 128/2 F
[58] Field of Search ................... 73/209; 128/2 F, 295

[56] References Cited

U.S. PATENT DOCUMENTS

| | | | |
|---|---|---|---|
| 2,648,981 | 8/1953 | Drake, Jr. | 128/2 X |
| 3,034,504 | 5/1962 | Winsor et al. | 73/209 X |
| 3,233,457 | 2/1966 | Martinez | 73/209 X |
| 3,769,497 | 10/1973 | Frank | 128/295 X |
| 3,803,914 | 4/1974 | Noiles | 73/209 |

*Primary Examiner*—Herbert Goldstein
*Attorney, Agent, or Firm*—Edmond T. Patnaude

[57] ABSTRACT

Instantaneous flow rates of a urine discharge are measured by a rotameter having a flexible conduit connected to the inlet of the rotameter.

5 Claims, 3 Drawing Figures

METHOD OF MEASURING THE INSTANTANEOUS FLOW RATE OF URINE DISCHARGE

The present invention relates in general to the art of metering the flow rate of a liquid discharge, and it relates more particularly to a new and improved method for making instantaneous measurements of the flow rate of a urinary discharge.

BACKGROUND OF THE INVENTION

Diagnosing of urological problems is facilitated by the analysis of information relating to the natural voiding of urine by the patient. Various instruments have been used in the past to measure such characteristics of the urine stream as total volume and average flow rate but no satisfactory instrument has been available for quickly and accurately indicating the instantaneous flow rate of the stream. However, such information and in particular the maximum flow rate of the urine stream is indicative of certain urological conditions. It is also important that the instrument provide repeatable measurements so that the progress of the patient can be monitored from time to time.

SUMMARY OF THE INVENTION

Briefly, in accordance with the present invention there is provided a new and improved method of metering the instantaneous voiding rate of a patient by the use of a rotameter having an open ended flexible conduit connected to the inlet at the bottom of the meter and an open ended conduit connected to the outlet at the top. With the open end of the flexible conduit held at a position above the outlet the conduit is filled with water until the meter and conduit are filled to the level of the outlet. Then as the patient voids into the enlarged funnel-like end of the flexible conduit, the instantaneous flow rate is indicated by the meter. A privacy screen may be positioned between the meter and the patient to avoid any psychological effect on the voiding rate due to the presence of the physician or technician who reads the meter.

GENERAL DISCRIPTION OF THE DRAWING

A better understanding of the present invention can be had by reference to the following detailed description, wherein.

DETAILED DESCRIPTION OF THE INVENTION

Figure 1:
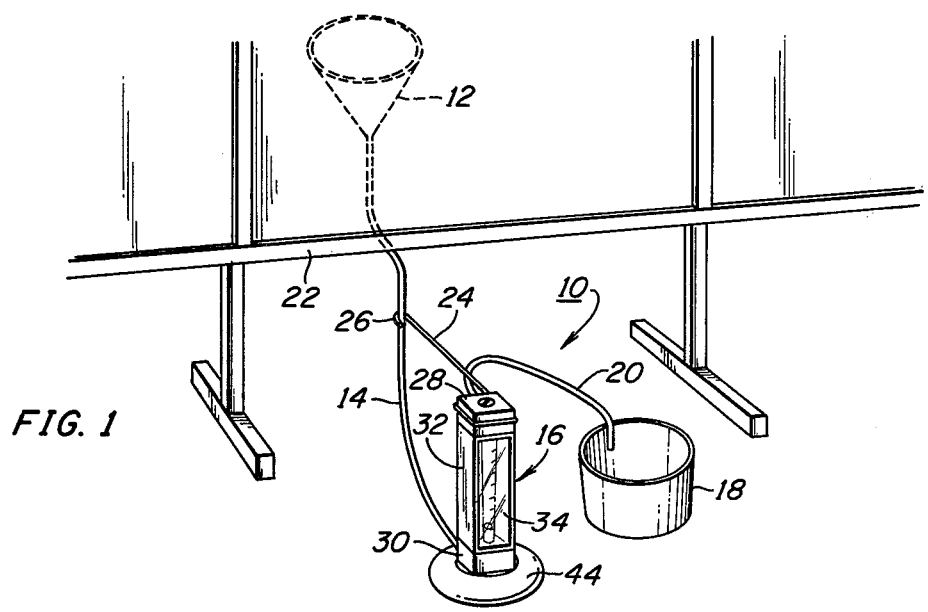
FIG. 1 is a perspective view of a voiding rate meter embodying certain aspects of the present invention.

Referring to FIG. 1, a system for metering the flow rate of urinary discharge is generally identified by the reference character 10 and includes as its principal elements an inlet funnel 12 connected by a flexible tube 14 to the inlet port of a conventional rotameter 16 having its outlet connected to a receptacle 18 by a tube 20. The tube may have an inner diameter of about one-quarter inch without substantially restricting the flow to the meter during a normal discharge. An opaque privacy screen 22 is shown positioned between the funnel 12 and the meter 16 so that while voiding the patient cannot be observed by the person reading the meter 10.

Figure 2:
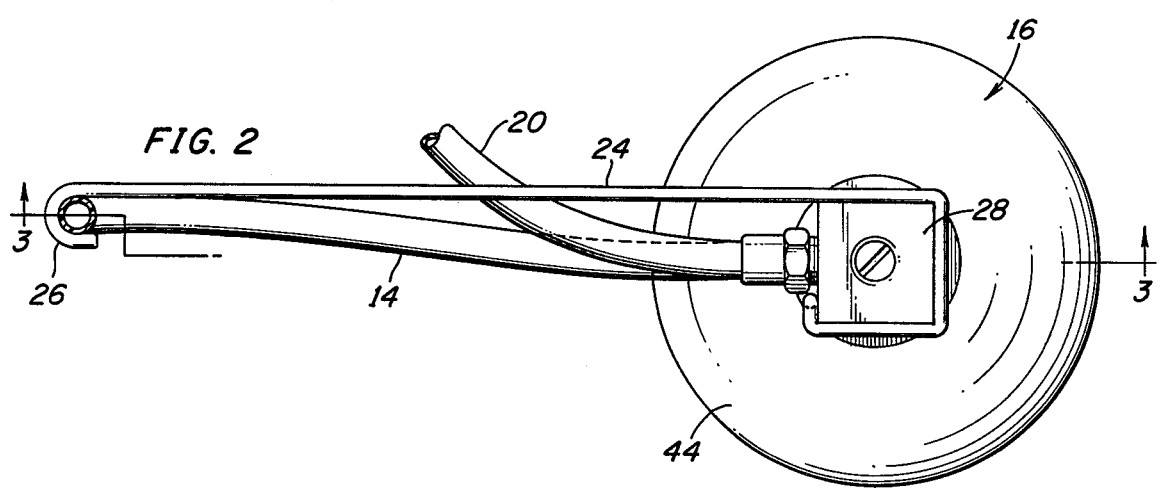
FIG. 2 is a top view of the meter portion of the device of FIG. 1.

A support arm 24 is removably attached to the housing of the meter and has a reversely bent hook-like outer end portion 26 for receiving the tube 14. The arm 24 is disposed at an elevation slightly higher than the outlet of the rotameter to prevent a reverse flow of liquid through the meter should the funnel 12 be inadvertently placed on the floor while the meter is filled with liquid. The arm 24 is preferably a metal rod which is removably fitted over the upper end of the meter 16 as best shown in FIGS. 2 and 3.

Figure 3:
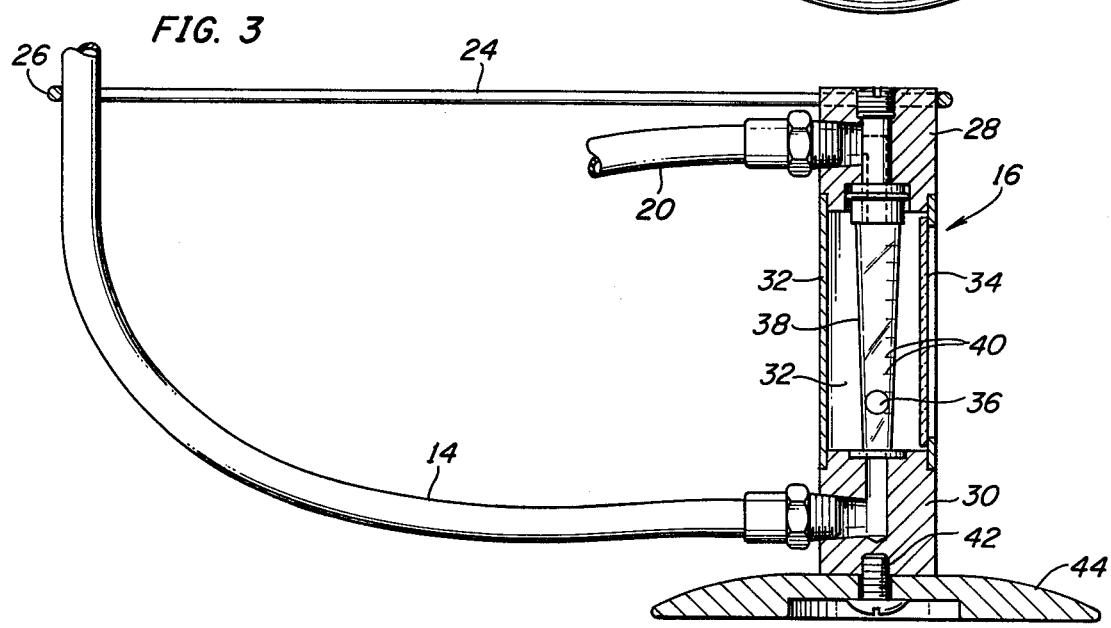
FIG. 3 is a cross-sectional view of the device of FIG. 2 taken along the line 3-3 thereof.

As best shown in FIG. 3, the rotameter 16 includes top and bottom end fittings 28 and 30 interconnected together by a plurality of plates 32. A transparent window 34 permits observation of a solid metal ball 36 disposed in a tapered, vertical metering tube 38 provided with graduation marks 40. The lower end of the tube 38 is connected to the tube 14, and the upper end of the tube 38 is connected to the tube 20. The lower fitting 30 is attached by a screw 42 to a base 44 which rests on the floor and holds the tube 38 in a vertical position.

While the flow meter 16 may be of any suitable construction, the system of the present invention has been used satisfactorily using a rotameter manufactured and sold by Ermerson Electric Co., under the name Kynar Sho-Rate 50.

When using the voiding rate meter of the present invention, the meter 44 is placed on the floor and separated from the patient by a privacy screen or wall. The distal end of the outlet tube 20 is placed in the receptacle 18. It is important that the distal end of the tube 20 not be inserted so far into the receptacle as to affect a siphon.

Water is then poured into the liquid discharge receptacle or funnel 12 until the tube 14 remains filled at the level of the outlet from the meter 16. Care should be taken at this time to eliminate air bubbles from the system. The funnel inlet receiver 12 is then held by the patient at a level of approximately 25 to 30 inches above the floor. Inasmuch as the instrument is slightly sensitive to variations in altitude pressure, children may be elevated on a short stool or the like during the voiding procedure.

As the patient voids into the funnel, the ball 36 immediately raises to a position in the tube related to the flow rate of urine into the tube 14. It has been found that the system 10 will provide repetitive instantaneous readings within $\frac{1}{4}$%. This has been determined by periodic measurements of the voiding rate of healthy persons having no urological problems.

After use, the system 10 may be easily and quickly cleaned in the following manner. The system is first flushed with tap water and thereafter, a solution of acetic acid or alcohol is flowed through the system to complete the cleaning process. If all parts of the rotameter 16 which are exposed to the liquid are fabricated of either 316SS or borosilicate glass, it is unnecessary to disassemble the rotameter for cleaning purposes.

The system thus provides a directly readable instantaneous reading of the voiding rate of a patient. No calculations are required nor are average or peak rate only measurements provided. Moreover, the metering system 10 has an accuracy of ±5% within a ten to one range of flow rates.

While the present invention has been described in connection with the particular embodiment thereof, it will be understood by those skilled in the art that many changes and modifications may be made without departing from the true spirit and scope of the present invention. Therefore, it is intended by the appended claims to cover all such changes and modifications which come within the true spirit and scope of this invention.

What is claimed:

1. A method of measuring the instantaneous flow rate of a urine discharge from a patient, comprising the steps of connecting one end of a conduit to the inlet of a rotameter having an inlet at the bottom and an outlet at the top, positioning the other end of said conduit at a location above the outlet of said rotameter, filling said conduit and said meter with an aqueous solution until the level of said solution in said conduit is at the same height as said outlet, and then causing said discharge to flow freely into said conduit during the voiding of urine by said patient, whereby said rotameter indicates the instantaneous flow rate of said discharge.

2. A method according to claim 1 wherein the cross-sectional area of said conduit is selected so as not to impede the free flow of said urine through said conduit to said rotameter.

3. A method according to claim 2 wherein said conduit is a flexible hose.

4. A method according to claim 2 comprising the additional step of positioning a visual barrier between said meter and said second end of said conduit.

5. A method according to claim 4 wherein said other end of said conduit is held at a predetermined height above the inlet during said voiding.

* * * * *